(12) United States Patent
Carvey et al.

(10) Patent No.: US 8,777,195 B2
(45) Date of Patent: Jul. 15, 2014

(54) NON-LINEAR TORSION SPRING ASSEMBLY

(75) Inventors: Matthew R Carvey, Somerville, MA (US); Andrew W Carvey, Cambridge, MA (US); Philip P Carvey, Bedford, MA (US); John A Rokosz, Belmont, MA (US); Nicholas S Howard, Bedford, MA (US)

(73) Assignee: Adicep Technologies, Inc., Bedford, MA (US)

( * ) Notice: Subject to any disclaimer, the term of this patent is extended or adjusted under 35 U.S.C. 154(b) by 126 days.

(21) Appl. No.: 13/243,333

(22) Filed: Sep. 23, 2011

(65) Prior Publication Data

US 2013/0075966 A1 Mar. 28, 2013

(51) Int. Cl.
*F16F 1/10* (2006.01)
(52) U.S. Cl.
USPC .......................................................... 267/156
(58) Field of Classification Search
USPC ................................................ 267/154–156
See application file for complete search history.

(56) References Cited

U.S. PATENT DOCUMENTS

| 209,642 | A | * | 11/1878 | Berlitz | 368/175 |
|---|---|---|---|---|---|
| 2,833,534 | A | * | 5/1958 | Foster | 267/156 |
| 3,884,449 | A | | 5/1975 | Kehm | |
| 4,776,574 | A | * | 10/1988 | Krambeck | 267/156 |
| 4,778,149 | A | | 10/1988 | Pesovic | |
| 5,080,640 | A | | 1/1992 | Botterill | |
| 5,195,693 | A | | 3/1993 | Sasaki | |
| 5,539,708 | A | | 7/1996 | Guignard | |
| 7,344,302 | B2 | * | 3/2008 | Musy et al. | 368/175 |
| 7,682,068 | B2 | * | 3/2010 | Bourgeois | 368/169 |
| 7,935,153 | B2 | | 5/2011 | Auberger | |
| 8,348,497 | B2 | * | 1/2013 | Daout | 368/175 |
| 2006/0142680 | A1 | | 6/2006 | Iarocci | |
| 2012/0008468 | A1 | * | 1/2012 | Bossart et al. | 368/175 |

* cited by examiner

*Primary Examiner* — Anna Momper

(74) *Attorney, Agent, or Firm* — The Patent Practice of Szmanda & Shelnut, LLC; Charles R. Szmanda; James G. Shelnut

(57) ABSTRACT

Disclosed and claimed herein are spiral torsion springs, non-linear torsion springs, and non-linear torsion spring assemblies. These devices are useful in damping applications, orthotic joint applications and servo control applications.

19 Claims, 5 Drawing Sheets

NON-LINEAR TORSION SPRING ASSEMBLY

FIELD OF THE INVENTION

The present disclosure is in the field of springs and spring assemblies, and more particularly in the field of spiral springs, non-linear springs, and non-linear spring assemblies.

BACKGROUND

A torsion spring is a type of spring that stores mechanical energy when a twisting force (torsion) is applied. These include torsion bars where the torsion is resisted by shear stresses, and spiral torsion springs wherein the torsion is resisted by bending stresses about the axis of their curvature. A spiral torsion spring has a coil portion with one or more coils usually forming a generally circular annulus with a coil axis and a transverse diameter generally perpendicular to the coil axis. When a torque is applied to a spiral torsion spring, an angular displacement between the first and second loading points is created, the coil deflects, and the material from which it is made is placed under stress. Spiral torsion springs may form a helix; a spiral; be flat, conical, spherical or volute in shape; or be less than a full coil; and are differentiated from compression and extensions springs by their application in resisting torsion.

A torsion spring can be linear or non-linear. In a linear torsion spring, the applied torque is directly proportional to the angular displacement via an unchanging variable called the spring rate. That is, the ratio between applied torque and angular displacement is constant. In a non-linear torsion spring, the applied torque and angular displacement are not proportional. There are two types of non-linear torsion springs, hardening and softening. In a hardening torsion spring, the ratio between applied torque and angular displacement grows such that with the application of an additional degree increase in angular displacement, more additional torque will be required than would be required for a linear spring. For example, in the simplest hardening spring, the ratio between applied torque and angular displacement equals $k_1 + k_2 \cdot \Theta$ where $k_1$ and $k_2$ are constants and $\Theta$ is the angular displacement. In a softening torsion spring, the amount of applied torque grows less than linearly.

Some systems provide a torsion spring having a series of holes along the spring axis that can be fixed to an end plate used to apply torque to the spring. This scheme allows a one-time adjustment of the length of the spring and thus its effective spring rate. While useful for matching the torque range to a particular application, the spring's applied torque is still directly proportional to the angular displacement because the spring's length does not change with applied torque.

Torsion springs are useful in a wide variety of applications including supplying power to mechanical devices such as clocks and toys, absorbing shock during motor startup and the like. While most torsion spring applications employ linear torsion springs, non-linear torsion springs are more suitable for some applications. For example, compound hunting bows, truck suspensions, and positioning applications in conjunction with servo controls where avoiding mechanical overshoot is desired, benefit through the non-linear properties while linear torsion springs generally do not help address the mechanical deficiencies.

Torsion springs provide for a relationship between torque and angular displacement. They can be used to simulate the relationship between torque and angular displacement of an existing mechanical system. Linear torsion springs can only replicate systems whose relationships are linear, while systems whose relationships are non-linear can only be replicated by non-linear torsion springs. As an example, a truck suspension employing a non-linear torsion spring is replicating an alternative system of compression springs, dampers, and linkages. Another system that has a non-linear relationship between torque and angular displacement is the human knee during ambulation with the torque provided by the quadriceps. In persons with deficient quadriceps, ambulation becomes difficult or impossible due to an inability to provide the necessary torque at sharper knee angles (larger angular displacements). Therefore, there exists a need for a system that can provide the non-linear relationship between torque and angular displacement of the human knee during ambulation. Further, there exists a need for a means of providing the non-linear relationship between torque and angle of the human knee during ambulation to those whose quadriceps are unable to provide that relationship.

SUMMARY OF THE DISCLOSURE

This disclosure introduces a solution to the problem of creating a non-linear torsion spring assembly capable of mimicking the relationship that exists between knee-torque and knee angle in an ambulating human.

In a first embodiment, a non-linear torsion spring assembly is disclosed. The non-linear torsion spring assembly comprises a torsion spring comprising an elastic material, an inner surface, an outer surface, an inner connection point, an outer connection point and a cross-section; a central support structure coupled to the inner connection point of the torsion spring and an outer support structure concentric to the central support structure coupled to the outer connection point of the torsion spring. The non-linear torsion spring assembly, the central support structure, the outer support structure or combinations thereof are configured so that, in operation, the effective spring length of the torsion spring changes as a function of the angular displacement between the central support structure and the outer support structure.

In a second embodiment, a spiral torsion spring is disclosed. The spiral torsion spring comprises an elastic bar coiled in a spiral around a center axis. The elastic bar has an outer surface, an inner surface and a cross section. A first portion of the spiral is defined by a first spiral function, a second portion of the spiral is defined by a second spiral function and each of the portions of the spiral is joined by a transitional portion.

In a third embodiment, a non-linear spiral torsion spring assembly is disclosed. The nonlinear spiral torsion spring assembly comprises a spiral torsion spring, comprising, an elastic material, an outer surface, an inner surface, a cross section, an inner connection point, and an outer connection point, a central support structure coupled to the inner connection point of the spiral torsion spring, and an outer support structure, concentric to the central support structure, coupled to the outer connection point. The non-linear spiral torsion spring assembly is configured so that, in operation, the inner surface of the spiral torsion spring maintains a point-to-point contact with the central support structure that shifts with increasing angular displacement between the central support structure and the outer support structure on their concentric axis, such that the effective spring length of the spiral torsion spring changes as a function of the angular displacement between the central support structure and the outer support structure, or the outer surface of the spiral torsion spring maintains a point to point contact with the interior of the outer support structure that shifts with increasing angular displacement between the central support structure and the outer support structure on their concentric axis, such that the effective spring length of the spiral torsion spring changes as a function of the angular displacement between the central support structure and the outer support structure. The point of contact between the inner support structure and the torsion spring and the point of contact between the outer support structure and the torsion spring may be either coplanar or out-of-plane.

In other embodiments, the spring assemblies or the springs of the above embodiments:
a. are spiral,
b. mimic the relationship that exists between knee angle and knee torque in an ambulating human,
c. are made from at least one elastic material, chosen from rubber; polymeric materials, such as, without limitation, polyester, polycarbonate, polyacrylates, polystyrenes, polyurethanes, polypropylenes, and polyolefins; metals, such as titanium, aluminum, cold rolled steel, tempered steel, carbon steel, austenitic stainless steel, precipitation hardened stainless steel, monel alloy 400, monel alloy K500, inconnel alloy 600, inconnel alloy x-750, cold worked copper brass, cold worked phosphor bronze, beryllium copper alloy, alloy steel, or composites comprising any of the foregoing. When the material is a metal, it may or may not be hardened or otherwise heat treated;
d. have a cross section and curvature along the spring's neutral axis selected to achieve a uniform maximum stress at all points of the inner and outer surfaces;
e. may further comprise voids along the neutral axis;
f. have a cross section of the torsion spring is chosen from rectangular, oval, triangular, circular, trapezoidal, T-beam or I-beam;
g. have a shape: chosen from an Archimedean spiral, a Fermat spiral, a hyperbolic spiral, a logarithmic spiral, a lituus spiral, a volute spiral, a helix, a conic helix, or a spherical spiral; that is either planar or three-dimensional; that comprises any number of turns;
h. have one or more step offsets; or
i. have predefined non-linear relationship between torque, and angular displacement between the support structures that mimics the relationship that exists between knee angle and knee torque in an ambulating humans.

In still other embodiments the support structures of the above embodiments are generally circular, ovular, elliptical or otherwise shaped to align closely with the first or final sections of the spiral torsion spring.

DETAILED DESCRIPTION

Figure 1:
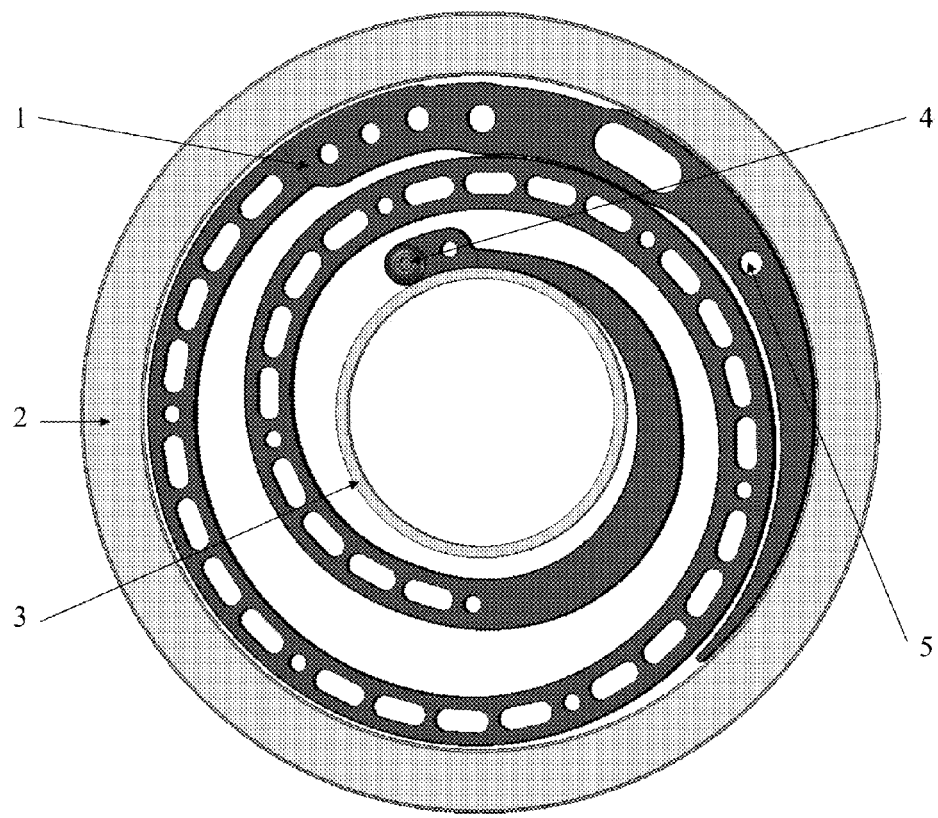
FIG. 1 illustrates a non-linear spiral torsion spring assembly showing a spiral torsion spring together with a central support structure and an outer support structure.

FIG. 1 shows a non-linear spiral torsion spring assembly with a spiral torsion spring, 1, an outer support structure, 2, an inner support structure, 3, an inner connection point, 4, with attachment means shown, and an outer connection point with attachment means not shown.

Figure 2:
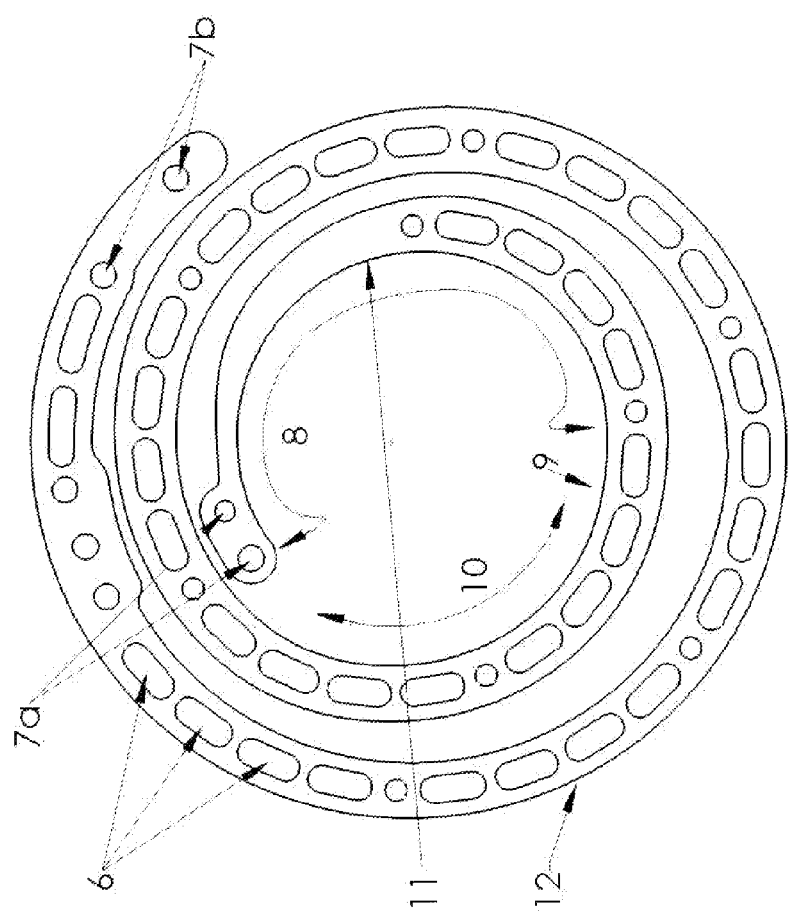
FIG. 2 illustrates a spiral torsion spring made of titanium containing a transition portion within the spring axis.

FIG. 2 shows a spiral torsion spring, designed to be made of titanium, provided with voids to reduce weight, 6 (also showing other voids along the spiral), holes to accommodate the inner connection point, 7a, and holes to accommodate the outer connection point, 7b, a first portion of the spiral torsion spring having a first defined shape, 8, a transitional portion between the first and second portion of the spiral torsion spring, 9, and a second portion of the spiral torsion spring, 10. Also shown are the inner surface, 11, and the outer surface, 12, of the spiral torsion spring.

Figure 3:
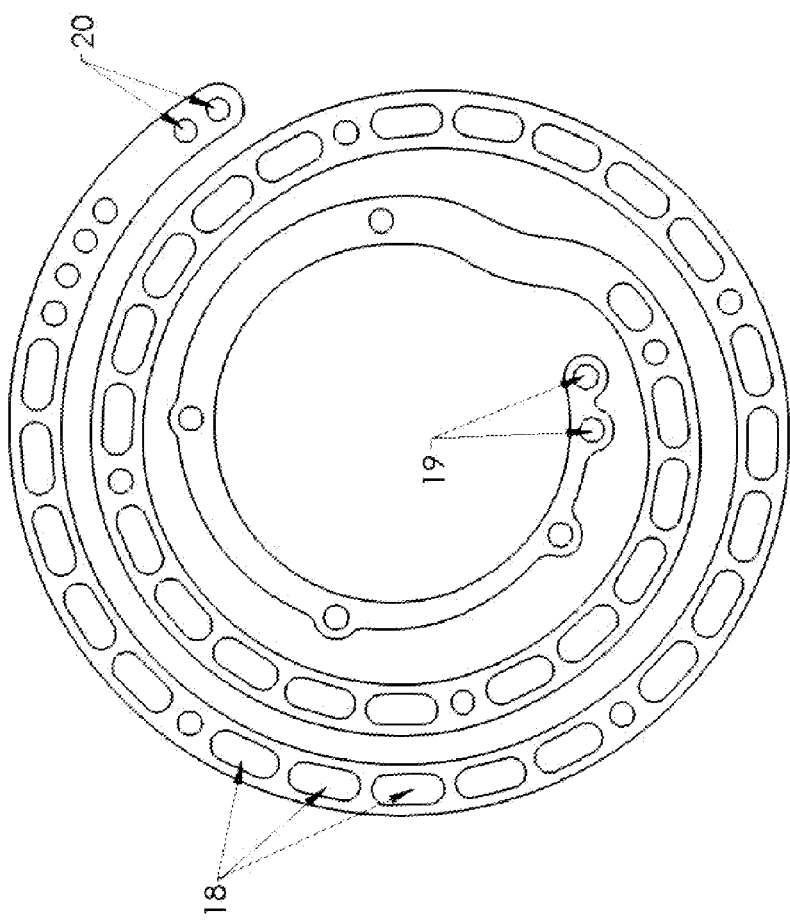
FIG. 3 illustrates a spiral torsion spring made of steel having a similar inner and outer mandrel size, and a similar non-linear torque vs. angular rotation profile as the titanium spring in FIG. 2.

FIG. 3 shows a spiral torsion spring designed to be made of made of steel having a similar inner and outer mandrel size and a similar non-linear torque vs. angular rotation profile as the titanium spring in FIG. 2. Shown are voids similar to those described supra, 18, holes to accommodate the inner connection point, 19, and holes to accommodate the outer connection point, 20. As is evident from the Figure, the overall shape of the spiral torsion spring designed to be made with steel differs from the overall shape of the spiral torsion spring with the same design criteria to be made with titanium.

Figure 4:
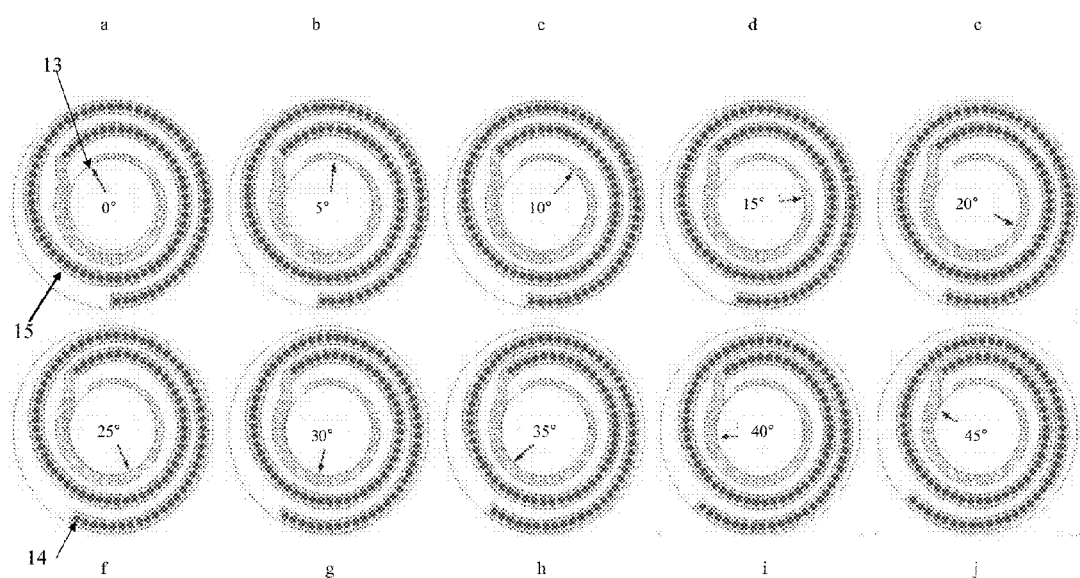
FIG. 4 illustrates the non-linear torsion spring assembly of FIG. 1 in operation showing the shifting position of the torque on the spring when various torques are applied to the outer support structure or central support structure.

FIG. 4 shows a schematic of a nonlinear spiral torsion spring assembly in which a spiral torsion spring, 15, is configured with an inner support structure, 13, and an outer support structure, 14. FIGS. 4a-4j represent various angular displacements, wherein the angles are 0°, 5°, 10°, 15°, 20°, 25°, 30°, 35°, 40°, and 45°, respectively and where the point-to-point contact is represented where the arrow is pointing. As can be seen as the angular displacement increase the point-to-point contact moves along the inner surface of the spring.

Figure 5:
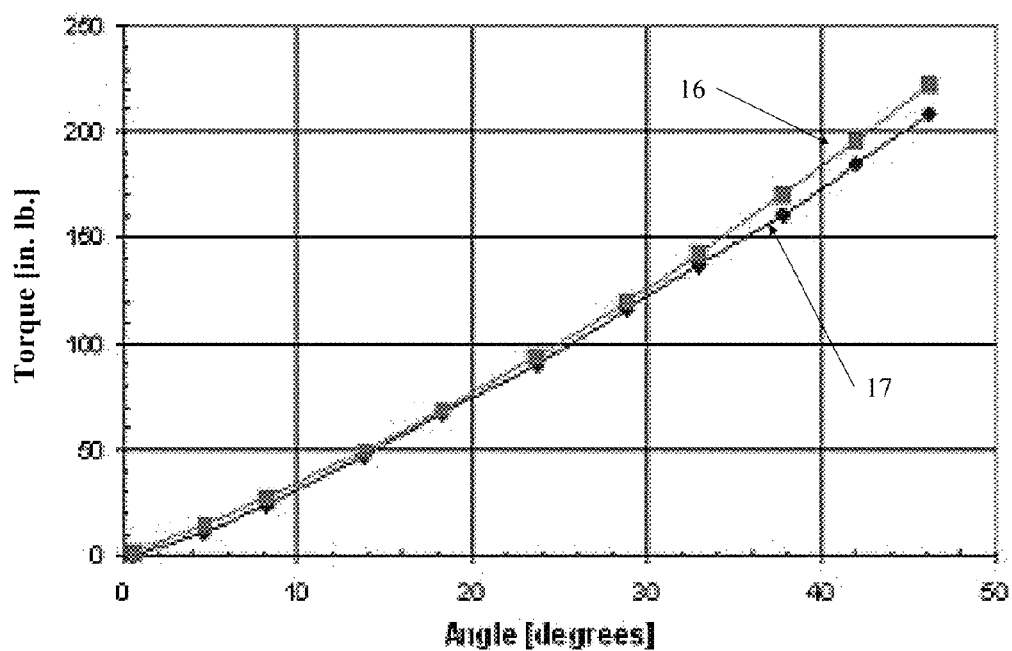
FIG. 5 illustrates the non-linear relationship between torque and angular displacement of the non-linear torsion spring assembly of FIG. 1.

FIG. 5 shows a plot of torque [in. lb.] vs. angle in degrees. Curve 16 shows the theoretical simulation while curve 17 shows experimental results for a non-linear spiral torsion spring assembly made with the specifications of the simulation.

As used herein, the conjunction "or" is understood to be inclusive unless otherwise stated. For example, the phrase "or alternatively" denotes an exclusive "or." As used herein, the word "exemplary" is intended to indicate an example and is not intended to indicate preference.

In certain embodiments, the non-linear torsion spring assembly, as shown in FIG. 1 comprises a spiral torsion spring 1, an outer support structure 2, and a central support structure 3. The spiral torsion spring may be shaped in any spring configuration, such as, for example, an Archimedean spiral, a Fermat spiral, a hyperbolic spiral, a logarithmic spiral, a lituus spiral, a volute spiral, a helix, a conic helix, a spherical spiral or combinations thereof, and may comprise any number of turns. The spiral torsion spring can be made from any material having a chosen elastic modulus for a given application wherein the elastic limit (whereby the spring deforms and does not return to its original position) is not reached. Useful materials include, for example, rubber; polymeric materials, such as, polyester, polycarbonate, polyacrylates, polystyrenes, polyurethanes, polypropylenes, and polyolephins; metals, such as titanium, aluminum, cold rolled steel, tempered steel, carbon steel, austenitic stainless steel, precipitation hardened stainless steel, monel alloy 400, monel alloy K500, inconnel alloy 600, inconnel alloy x-750, cold worked copper brass, cold worked phosphor bronze, beryllium copper alloy, alloy steel; or composite materials comprising any of the foregoing.

Combinations of spiral spring configurations may also be employed. For example, two different Archimedean spirals, joined by a transitional portion, may be incorporated into a spiral spring.

Metals used in these applications may be hardened or otherwise heat-treated. Exemplary heat-treating conditions are shown Table 1.

TABLE 1

| Spring Materials | Heat Treatment | |
|---|---|---|
| | °C. | °F. |
| Cold Drawn steel Wire | 190-230 | 375-450 |
| Tempered Steel Wire: | | |
| Carbon | 260-400 | 500-750 |
| Alloy | 315-425 | 600-800 |
| Austenitic Stainless Steel wire | 230-510 | 450-950 |
| Precipitation Hardening Stainless Wire (17-7 PH): | | |
| Condition C | 480/1 hour | 900/1 hour |
| Condition A to TH 1050 | 760/1 hour cool to 15 followed by 565/1 hour | 1400/1 hour cool to 60 followed by 1050/1 hour |
| Monel: | | |
| Alloy 400 | 300-315 | 575-600 |
| Alloy K500, Spring Temper | 525/4 hours | 980/4 hours |
| Inconnel: | | |
| Alloy 600 | 400-510 | 750-950 |
| Alloy X-750: | | |
| #1 Temper | 730/16 hours | 1350/16 hours |
| Spring Temper | 650/4 hours | 1200/4 hours |
| Copper Base, Cold Worked (Brass, Phosphor Bronze, etc.) | | |
| Beryllium Copper: | 175-205 | 350-400 |
| Pretempered (Mill Hardened) | 205 | 400 |
| Solution Annealed, Temper Rolled or Drawn | 315/2-3 hours | 600/2-3 hours |
| Annealed Steels: | | |
| Carbon (AISI 1050 to 1095) | 800-830* | 1475-1525* |
| Alloy (AISI 5160 H 6150, 9254) | 830-885* | 1525-1625* |

*Time depends on heating equipment and section size. Parts are austenized then quenched and tempered to the desired hardness As an example of heat-treating, an austempering process can be used. Spiral springs of 6150 or 5160 steel are fabricated. The steel is heated to its eutectic point, approximately 855° C., and is then quenched in a salt bath held at approximately 300-400° C. Without intending to be bound by theory it is believed that, after such austempering, the steel is in a banite state allowing for desirable flexibility and strength.

For some applications, the material choice should be sufficiently robust to withstand at least tens of millions of work cycles, such as would be beneficial in a knee joint application. The material should also exhibit a suitably long stress-strain curve over the intended load cycle.

The spiral torsion spring may have a cross section shape including, for example, rectangular, oval, triangular, circular, trapezoidal, T-beam, or I-beam. Furthermore, a non-uniform cross-section may be employed, varying by either or both shape and cross-sectional area along the spiral.

In many applications it is desirable to reduce the weight of the spiral torsion spring as much as possible. However making the spring very thin in order to reduce its weight may cause the spring to have reduced strength. To address this, the spring of the present disclosure as shown in FIG. 2 may have one or more voids 6 situated along the spiral portion of the spring. Voids are created by removing material at various positions along the spring. This allows the spring to retain its strength while reducing weight. As the material nearest the centerline of a torsion spring stores essentially no energy, cutting slots along the centerline reduces weight, while the nominally reduced energy storage can be restored by slightly increasing thickness, thus maintaining the original torque profile. This slotting technique may reduce weight by as much as 40%.

In other applications it may be desirable to adjust the length of the spiral torsion spring in relation to the expected load. This allows for predefining the non-linear relationship between the torque and the angular displacement between the central support structure and the outer support structure of the spring assembly. For example if an initial load is predefined to be a light load, the connection point will be at the end of the spring, be it situated on the inner portion of the spring or the outer portion of the spring. Conversely, for an initial load that is predefined to be a heavy load, the connection point can be at a point further along the spring and thus shortening the spring. The spring of the present disclosure may thus have more than one attachment point 7 along the spiral spring to allow the spring to be coupled to other hardware The spiral torsion spring of the present application may further have an angular spiral function with a step offset in which the angular spiral function shifts through a transition from one angular spiral function to another. For example, an Archimedean spiral has an angular spiral function characterized by the following equation:

$$r = a + b \cdot \theta$$

A step offset may be fabricated by forming a first portion of the spiral torsion spring 8 with selected values of a and b, introducing a transitional portion 9, and continuing to form the spring with a second portion 10 with different values of a or b. It should be noted that when employing an angular spiral function the spring need not take the shape of an Archimedean spiral but can be, for example, an Euler spiral, a Cornu spiral, a Fermat spiral, a hyperbolic spiral, a lituus spiral, a logarithmic spiral or a spiral of any other spiral function. The respective functions defining the aforementioned spiral forms are similarly characterized by their own sets of constants.

The central support structure of the non-linear torsion spring assembly may be configured with the spring in a number of different ways. In one example, at least one point of the inner surface of the inner turn of the spiral torsion spring 11 is positioned on the central support structure. The central support structure may be coupled to an anchoring member such as, for example, a support platform or other support device. The spring is coupled to the central support structure, the support platform, or both at an inner connection point 4 by various attachment means. Attachment means include for example, screws, bolts, rivets, cotter-pins, welds, solder joints, press fittings, magnetic fittings, pegs, mold fittings, welds and the like as well as unitary construction in which the spring and at least some of the supporting hardware are formed from the same piece of material. By using the word "coupled" it is contemplated that an object can be fastened by techniques known in the art or that the object can be formed in one piece with a second object. In the present instance, the central support structure can be coupled to the anchoring member using rivets, screws, nuts and bolts, welds, solder joints, clamps, press fittings, magnetic fittings and the like. In addition, the central support structure and the anchoring member can be fashioned as a single unit wherein they are formed from the same piece of material. The shape of the central support structure may be generally circular, ovular, elliptical or other shapes that allow the inner surface of the inner turn of the spring to make contact, point-to-point or otherwise, such that the desired torque displacement function is achieved The outer support structure of the non-linear torsion spring assembly can also be configured in a number of different ways. In one example, at least one point of the outer surface of the outer turn of the spiral torsion spring 12 is positioned on the outer support structure. The spring is coupled to the outer support structure by attachment means or tension fitting at the outer connection point 5. Attachment means include for example, screws, bolts, rivets, cotter-pins, welds, solder joints, press fittings, magnetic fittings, pegs, mold fittings and the like as well as unitary construction in which the spring and at least some of the supporting hardware are formed from the same piece of material. The shape of the outer support structure may be generally circular, ovular, elliptical or other shapes that allow the outer surface of the outer turn of the spring to make contact, point-to-point or otherwise.

The central support structure and the outer support structure are configured to move relative to each other and independently from each other. Thus, in some applications, the central support structure may be stationary while the outer support structure freely rotates, or the outer support structure may be stationary while the central support structure rotates. In other applications both the central support structure and the house may be free to rotate.

The spiral torsion spring of the non-linear torsion spring assembly may be chosen to be planar or may have one or more portions that are out-of-plane.

In a first example of the spiral support assembly in operation, the inner turn of the spiral torsion spring is coupled to the central support structure or an anchoring member to which the central support structure is also coupled and the outer portion of the spring is coupled to the outer support structure. As illustrated in FIG. 4, the inner surface of the spring makes a point-to-point contact 13, with the central support structure. FIG. 4a is the initial, neutral position, prior to any torque applied to the spring. As the outer support structure or central support structure rotates, a torque is applied to the spiral torsion spring and the spring wraps itself around the central support structure, causing the point-to-point contact to shift to a different position on the spring, FIG. 4b; thus altering the location of the torque on the spring and thereby the effective spring length. In FIGS. 4a-4j the arrows inside the springs indicate the position of the point-to-point contact, and the point on the spring to which the torque will be applied. As more torque is applied to the outer connection point of the spring 14, the point-to-point contact shifts to different positions around the central support structure. FIGS. 4a-4j illustrate the shifting of the point-to-point contact—the location of the torque on the spring—as more torque is applied to the spring and the overall effective length of the spring shortens.

FIG. 5 illustrates the theoretical and measured relationship between the torque and the angular displacement. Initially the torque is zero when the angular displacement between the diameter of the outer support structure and the central support structure is zero. This position on the graph corresponds to illustration in FIG. 4a. As the angular displacement increases the torque increases. As the graph demonstrates, the increase in torque increases non-linearly as a function of angular displacement. FIG. 5 illustrates the theoretical 16 (simulated data) and measured 17 (experimental data) torque vs. angular displacement profiles.

In the spring of the present disclosure the step offset allows only the inner surface of the inner turn of the spiral torsion spring to create a shifting point-to-point contact with the central support structure. This inhibits point-to-point contact between the outer support structure and the outer surface of the spring or between the surfaces of the spring itself, reducing the complexity introduced by multiple point-to-point contacts and thereby requiring less tight manufacturing tolerances.

In a second example of the non-linear torsion spring assembly in operation, the spiral torsion spring is coupled to the central support structure or an anchoring member to which the central support structure is also coupled, the outer turn of the spring is coupled to the outer support structure, and the outer surface of the outer turn of the spring makes a point-to-point contact with the outer support structure. The point of contact between the outer surface of the spring and outer support structure is the location of the load on the spring. As the outer support structure or the central support structure rotates, torque is applied to the spring and the spring uncurls causing the point-to-point contact to shift to a different position on the spring. As more torque is applied to the spring, the point-to-point contact continues to shift to progressively advanced positions around the outer support structure. Similar to the first example, the shifting point-to-point contact shortens the effective spring length, allowing for a non-linear relationship between the torque and angular displacement of the outer support structure and the central support structure. Again the step offset allows for only the outer surface of the spring and the inner surface of the outer support structure to create a shifting point-to-point contact.

In a third example of the non-linear torsion spring assembly in operation, the inner turn of the spiral torsion spring is coupled to the central support structure or an anchoring member to which the central support structure is also coupled, the outer turn of the spring is coupled to the outer support structure, and the spring is constructed so as to make a point-to-point contact between the inner surface of the spring and the outer surface of an interior coil of the spring at certain degrees of angular displacement. As the outer support structure or central support structure rotates, a torque is applied to the spring and the spring wraps itself around itself causing the point-to-point contact to shift to progressively advanced positions on the spring thus shortening the effective spring length. This contact may or may not be subsequent to, prior to, or concurrent with shifting point-to-point contacts between the outer surface of the spring and the inner surface of the outer support structure, and may or may not be subsequent to, prior to, or concurrent with shifting point-to-point contacts between the inner surface of the spring and the outer surface of the inner support structure. The point of contact between the inner surface of the spring and the outer surface of the spring is the location of the torque on the spring. As more torque is applied to the spring, the point-to-point contact continues to shift to different positions around the spring.

The initial coupling points of the spiral torsion spring to the outer support structure and/or the central support structure may be adjusted depending on what the intended load is going to be. For example, coupling the spring at its most terminal point will allow one torque vs. angular displacement relationship. If the spring is coupled at positions that shorten the spring, the torque vs. angular displacement relationship will change. If the spring is coupled so that the spring is effectively shortened, the torque vs. angular displacement relationship will be steeper, that is, as the angular displacement is increased, the torque will increase at a higher rate than when the spring is not effectively shortened. In this way the non-linear torsion spring assembly can be customized to provide the best support depending on the intended load and a predefined non-linear relationship between the torque and the angular displacement of the central support structure and the outer support structure can be obtained.

The choice of shape and materials will determine the non-linear relationship between torque and angular displacement between the central support structure and the outer support structure. For example, a spring made of titanium, as illustrated in FIG. 2 having the shape shown and the corresponding circular support structures, will have the torque profile shown in FIG. 5. A second spring made of austempered steel, with its significantly different spring properties, can be shaped, as illustrated in FIG. 3, to be used with the same support structures while having the identical torque profile via a different spiral function.

The non-linear relationship between torque and angular displacement between the central support structure and the outer support structure can be chosen to replicate torque vs. angular displacement relationships found in nature such as the relationship between knee angle and the knee torque applied by a normally functioning quadriceps in an ambulating human. By mimicking the knee-torque vs. knee-angle relationship, when employed in a structure that attaches above and below the knee, the non-linear torsion spring assembly can be used to provide knee torque that can substitute for the function of the quadriceps.

The present disclosure has been described in connection with various embodiments. Notwithstanding the foregoing, it should be understood that modifications, alterations, and additions can be made to the subject of the present disclosure without departing from the scope of the subject of the present disclosure as defined by the appended claims.

We claim:

1. A non-linear spiral torsion spring assembly comprising:
 a. a spiral torsion spring comprising: an elastic material; an inner surface; an outer surface; a neutral axis; an inner connection point; an outer connection point; and a cross-section
 b. a central support structure coupled to the inner connection point of the spiral torsion spring; and
 c. an outer support structure concentric to the central support structure coupled to the outer connection point of the spiral torsion spring;
 d. wherein said non-linear spiral torsion spring assembly is configured so that, in operation:
  i. the inner surface of the spiral torsion spring contacts a point on the central support structure forming a point-to-point contact that shifts with increasing angular displacement between the central support structure and the outer support structure on their concentric axis such that the effective spring length of the spiral torsion spring changes as a function of the angular displacement between the central support structure and the outer support structure; or
  ii. ii. the outer surface of the spiral torsion spring contacts a point on the interior of the outer support structure forming a point to point contact that shifts with increasing angular displacement between the central support structure and the outer support structure on their concentric axis such that the effective spring length of the spiral torsion spring changes as a function of the angular displacement between the central support structure and the outer support structure,
 e. wherein, the point of contact between the central support structure and the torsion spring and the point of contact between the outer support structure and the torsion spring may be either coplanar or out of plane, wherein the cross section of the spring along the neutral axis is nonuniform, and wherein the cross section and curvature along the spring's neutral axis achieves a uniform maximum stress at all points of the inner and outer surfaces.

2. A non-linear torsion spring assembly comprising:
 a. a torsion spring comprising: an elastic material; an inner surface; an outer surface; an inner connection point; an outer connection point; a neutral axis; and a cross-section;
 b. a central support structure coupled to the inner connection point of the torsion spring; and
 c. an outer support structure concentric to the central support structure coupled to the outer connection point of the torsion spring;
 wherein the torsion spring, the central support structure, the outer support structure, or combinations thereof are configured so that in operation the effective spring length of the torsion spring changes as a function of the angular displacement between the central support structure and the outer support structure, wherein the torsion spring, the central support structure, the outer support structure, or combinations thereof are configured so that in operation a predefined non-linear relationship exists between torque and angular displacement between the central support structure and the outer support structure, wherein the cross section of the spring along the neutral axis is nonuniform, and wherein the cross section and curvature along the spring's neutral axis achieves a uniform maximum stress at all points of the inner and outer surfaces.

3. The non-linear torsion spring assembly of claim 2, wherein the central and outer support structures are concentric and angular displacement between the central support structure and the outer support structure is on their concentric axis.

4. The non-linear torsion spring assembly of claim 2, wherein the central support structure and the outer support structure are free to rotate relative to or independent of each other.

5. The non-linear torsion spring assembly of claim 2, further comprising voids along the neutral axis of the torsion spring.

6. The non-linear torsion spring assembly of claim 2, wherein the elastic material is rubber, polyester, polycarbonate, polyacrylate, polystyrene, polyurethane, polypropylene, and polyolephin, titanium, aluminum, cold rolled steel, tempered steel, carbon steel, austenitic stainless steel, precipitation hardened stainless steel, monel alloy 400, monel alloy K500, inconnel alloy 600, inconnel alloy x-750, cold worked copper brass, cold worked phosphor bronze, beryllium copper alloy, alloy steel; or a composite comprising any of the foregoing.

7. The non-linear torsion spring assembly of claim 2, wherein the cross section is rectangular, oval, triangular, circular, trapezoidal, T-beam or I-beam.

8. The non-linear torsion spring assembly of claim 2, wherein the spiral torsion spring's shape is an Archimedean spiral, a Fermat spiral, a hyperbolic spiral, a logarithmic spiral, a lituus spiral, a volute spiral, a helix, a conic helix, or a spherical spiral; and wherein the torsion spring is either planar or three-dimensional.

9. The non-linear torsion spring assembly of claim 2, wherein the spiral torsion spring has at least one step offset wherein a first portion of the torsion spring is defined by a first spiral function, an at least one additional portion of the spiral torsion spring is defined by an at least one additional spiral function and the consecutive portions of the spiral torsion spring are joined by transitional portions.

10. The non-linear torsion spring assembly of claim 9, wherein the central support structure is generally circular, ovular, elliptical or otherwise shaped to closely align with the first section of the spiral torsion spring.

11. The non-linear torsion spring assembly of claim 2, wherein the inner surface of the spiral torsion spring contacts a point on the central support structure forming a point-to-point contact that shifts with increasing angular displacement between the central support structure and the outer support structure.

12. The non-linear torsion spring assembly of claim 2, wherein the outer surface of the spiral torsion spring contacts a point on the outer support structure forming a point to point contact that shifts with increasing angular displacement between the central support structure and the outer support structure.

13. The non-linear torsion spring assembly of claim 2, wherein the inner surface of the spiral torsion spring contacts a point on the outer surface of the spiral torsion spring forming a point-to-point contact that shifts with increasing angular displacement between the central support structure and the outer support structure.

14. A non-linear torsion spring assembly comprising:
  a. a torsion spring comprising: an elastic material; an inner surface; an outer surface; an inner connection point; an outer connection point; a neutral axis; and a cross-section;
  b. a central support structure coupled to the inner connection point of the torsion spring; and
  c. an outer support structure concentric to the central support structure coupled to the outer connection point of the torsion spring;
wherein the torsion spring, the central support structure, the outer support structure, or combinations thereof are configured so that in operation the effective spring length of the torsion spring changes as a function of the angular displacement between the central support structure and the outer support structure, wherein the torsion spring, the central support structure, the outer support structure, or combinations thereof are configured so that in operation a predefined non-linear relationship exists between torque and angular displacement between the central support structure and the outer support structure, wherein the cross section of the spring along the neutral axis is nonuniform, and wherein the non-linear relationship between torque, and angular displacement between the central support structure and the outer support structure, mimics the relationship that exists between knee angle and knee torque in an ambulating human by mimicking the knee-torque vs. knee angle relationship, when employed in a structure that attaches above and below the knee.

15. The non-linear torsion spring assembly of claim 14, wherein the central and outer support structures are concentric and angular displacement between the central support structure and the outer support structure is on their concentric axis.

16. The non-linear torsion spring assembly of claim 14, wherein the central support structure and the outer support structure are free to rotate relative to or independent of each other.

17. The non-linear torsion spring assembly of claim 14, wherein the cross section is rectangular, oval, triangular, circular, trapezoidal, T-beam or I-beam.

18. The non-linear torsion spring assembly of claim 14, wherein the spiral torsion spring's shape is an Archimedean spiral, a Fermat spiral, a hyperbolic spiral, a logarithmic spiral, a lituus spiral, a volute spiral, a helix, a conic helix, or a spherical spiral; and wherein the torsion spring is either planar or three-dimensional.

19. The non-linear torsion spring assembly of claim 14, wherein the spiral torsion spring has at least one step offset wherein a first portion of the torsion spring is defined by a first spiral function, an at least one additional portion of the spiral torsion spring is defined by an at least one additional spiral function and the consecutive portions of the spiral torsion spring are joined by transitional portions.

* * * * *